US007889954B2

(12) United States Patent
Sailor et al.

(10) Patent No.: US 7,889,954 B2
(45) Date of Patent: Feb. 15, 2011

(54) OPTICAL FIBER-MOUNTED POROUS PHOTONIC CRYSTALS AND SENSORS

(75) Inventors: Michael J. Sailor, La Jolla, CA (US); Brian H King, LaJolla, CA (US); Anne M Ruminski, El Centro, CA (US); Jay L Snyder, Jefferson Hills, PA (US)

(73) Assignee: The Regents of the University of California, Oakland, CA (US)

( * ) Notice: Subject to any disclaimer, the term of this patent is extended or adjusted under 35 U.S.C. 154(b) by 134 days.

(21) Appl. No.: 12/218,330

(22) Filed: Jul. 14, 2008

(65) Prior Publication Data

US 2010/0008619 A1    Jan. 14, 2010

Related U.S. Application Data

(60) Provisional application No. 60/959,210, filed on Jul. 12, 2007.

(51) Int. Cl.
*G02B 6/00* (2006.01)
(52) U.S. Cl. .......................................... 385/12; 385/13
(58) Field of Classification Search .................. 385/12, 385/13
See application file for complete search history.

(56) References Cited

U.S. PATENT DOCUMENTS

| | | | |
|---|---|---|---|
| 4,834,496 A | 5/1989 | Blyler, Jr. et al. | |
| 5,244,636 A | 9/1993 | Walt et al. | |
| 5,250,264 A | 10/1993 | Walt et al. | |
| 5,338,415 A | 8/1994 | Sailor et al. | |
| 6,266,459 B1 | 7/2001 | Walt et al. | |
| 6,375,725 B1 | 4/2002 | Bernard et al. | |
| 6,535,658 B1 * | 3/2003 | Mendoza et al. | 385/12 |
| 6,590,647 B2 * | 7/2003 | Stephenson | 356/301 |
| 6,897,965 B2 * | 5/2005 | Ghadiri et al. | 356/519 |

(Continued)

FOREIGN PATENT DOCUMENTS

WO    WO 03/067231    8/2003

(Continued)

OTHER PUBLICATIONS

K.J. Albert, D.R. Walt, D.S. Gill, T.C. Pearce, "Optical Multibead Arrays for Simple and Complex Odor Discrimination", *Anal. Chem.* vol. 73, p. 2501-2508.

(Continued)

*Primary Examiner*—Ellen Kim
(74) *Attorney, Agent, or Firm*—Greer, Burns & Crain Ltd.

(57) ABSTRACT

An embodiment of the invention is a remote sensor that has an optical fiber terminating in a tip. A thin film porous particle having a characteristic optical response that changes in the presence of an analyte is optically coupled and physically attached to the tip of the optical fiber. The optical response of the particle changes in the presence of analyte, and the particle also serves to concentrate analyte. The thin film porous particle can be functionalized toward sensitivity for a predetermined analyte or analytes. A method of remote sensing exposes the remote sensor to an environment to be monitored for analyte. The thin film porous particle is probed with a beam of light. Reflected light is monitored through the optical fiber for a shift in frequency or intensity.

17 Claims, 6 Drawing Sheets

U.S. PATENT DOCUMENTS

| | | | |
|---|---|---|---|
| 7,042,570 | B2 | 5/2006 | Sailor et al. |
| 7,318,903 | B2 * | 1/2008 | Link et al. .................. 216/2 |
| 2002/0191884 | A1 * | 12/2002 | Letant et al. ................ 385/12 |
| 2003/0112443 | A1 * | 6/2003 | Hjelme et al. ............... 356/480 |
| 2003/0146109 | A1 | 8/2003 | Sailor et al. |
| 2005/0009374 | A1 | 1/2005 | Gao et al. |
| 2005/0042764 | A1 | 2/2005 | Sailor et al. |
| 2005/0163650 | A1 * | 7/2005 | Crawford et al. ............... 422/4 |
| 2005/0177035 | A1 * | 8/2005 | Botvinick et al. ........... 600/347 |
| 2005/0196317 | A1 * | 9/2005 | Walt et al. ..................... 422/57 |
| 2006/0227330 | A1 * | 10/2006 | Hjelme et al. ............... 356/481 |
| 2006/0255008 | A1 | 11/2006 | Sailor et al. |
| 2007/0051815 | A1 | 3/2007 | Sailor et al. |
| 2007/0108465 | A1 | 5/2007 | Sailor et al. |
| 2007/0148695 | A1 | 6/2007 | Sailor et al. |
| 2008/0119701 | A1 * | 5/2008 | Milner et al. ............... 600/342 |
| 2008/0145513 | A1 | 6/2008 | Sailor |
| 2009/0075229 | A1 * | 3/2009 | Rizoiu et al. ................. 433/29 |
| 2009/0260423 | A1 * | 10/2009 | Munoz et al. ............. 73/61.71 |
| 2009/0298004 | A1 * | 12/2009 | Rizoiu ......................... 433/29 |
| 2009/0298391 | A1 * | 12/2009 | Yamada ........................ 451/41 |
| 2009/0311144 | A1 * | 12/2009 | Kim et al. ................... 422/119 |

FOREIGN PATENT DOCUMENTS

| | | |
|---|---|---|
| WO | WO2005/062865 | 12/2004 |
| WO | WO 2005/034725 | 4/2005 |

OTHER PUBLICATIONS

E.J. Anglin, L. Cheng, W.R. Freeman, M.J. Sailor, "Porous Silicon in Drug Delivery Devices and Materials", *Advanced Drug Delivery Reviews*, vol. 60, 2008, pp. 1266-1277.

S. M. Barnard, D. R. Walt, "Fiber-Optic Organic Vapor Sensor", *Environ. Sci. Technol.* 1991, vol. 25, p. 1301.

S. Caron, P. Bernard, M. Vernon, J. Lara, "Porous Glass Optical Fiber Sensor as an End-of-Service Indicator for Respiratory Cartridges" *Sensors and Actuators B: Chemical* 2004, vol. 102, p. 198-206.

G. Favas, "End of Service Life Indictor (ESLI) for Respirator Cartridges. Part I: Literature Review", Australian Government Department of Defense, DSTO-TN-0657, 2005.

T. Gao, 1. Gao, MJ. Sailor, "Tuning the Response and Stability of Thin Film Mesoporous Silicon Vapor Sensors by Surface Modification", *Langmuir* 2002, vol. 18, p. 9953.

B. Lee, "Review of the Present Status of Optical Fiber Sensors", *Optical Fiber Technology* 2003, vol. 9, p. 57.

B. D. MacCraith, C. M. McDonagh, G. O'Keeffe, E. T. Keyes, J. G. Vos, B. O'Kelly, J. F. McGlip, "Fibre Optic Oxygen Sensor Based on Fluorescence Quenching of Evanescent-wave Excited Ruthenium Complexes in Sold-Gel Derived Porous Coatings", *Analyst* 1993, vol. 118, p. 385.

F. Mitschke, "Fiber-Optic Sensor for Humidity", *Optics Letters* 1989, vol. 14, p. 967.

D. Monzon-Hernandez, J. Villatoro, D. Luna-Moreno, "Miniature Optical Fiber Refractometer Using Cladded Multimode Tapered Fiber Tips", *Sensors and Actuators B: Chemical* 2005, vol. 110, p. 36.

E. S. Moyer, M. W. Findlay, G. J. Maclay, J. R. Stetter, "Preliminary Evaluation of an Active End-of-Service-Life Indicator for Organic Vapor Cartridge Respirators", *American Industrial Hygiene Association journal* 1993, vol. 54, p. 417.

M.J. Sailor, J.R. Link, "Smart dust": Nanostructured Devices in a Grain of Sand, *Chern. Commun.* 2005, p. 1375.

H. Suzuki, M. Sugimoto, Y. Matsui, J. Kondoh, "Development of a dual-color optical fiber SPR sensor", *Sensors, 2005 IEEE*, 2005, p. 865.

S. Tanaka, Y. Tsuda, S. Kitamura, M. Shimada, H. Arito, Y. Seki, "A Simple Method for Detecting Breakthroughs in Used Chemical Cartridges", *AIHAJ—American Industrial Hygiene Association* 2001, vol. 62, p. 168.

C. M. Tay, K. M. Tan, S. C. Tjin, C. C. Chan, H. Rahardjo, "Humidity sensing using plastic optical fibers", *Proceedings of the SPIE 2004*, vol. 5590, p. 77.

A. Wang, G. Z. Wang, K. A. Murphy, R. O. Claus, "Fiber-Optic Temperature Sensors Based on Differential Spectral Transmittance/ Reflectivity and Multiplexed Sensing Systems", *Applied Optics* 1995, vol. 34, p. 2295.

O. S. Wolfbeis, "Materials for Fluorescence-Based Optical Chemical Sensors", *J. Mater Chern.* 2005, vol. 15, p. 2657.

G. Z. Xiao, A. Adnet, Z. Zhang, F. G. Sun, C. P. Grover, "Monitoring Changes in the Refractive Index of Gases by Means of a Fiber Optic Fabry-Perot Interferometer Sensor", *Sensors and Actuators A: Physical* 2005, 118,177.

Q. Zhou, D. Kritz, L. Bonnell, G. H. Siegel, "Porous Plastic Optical Fiber Sensor for Ammonia Measurement", *Applied Optics* 1989, vol. 28, p. 2022.

* cited by examiner

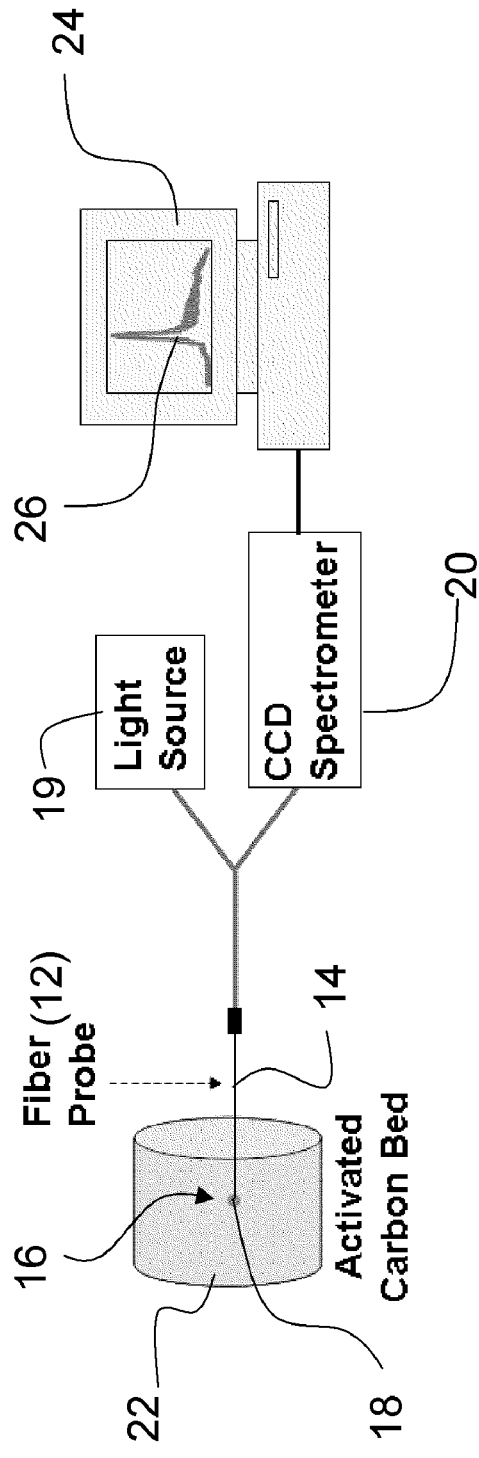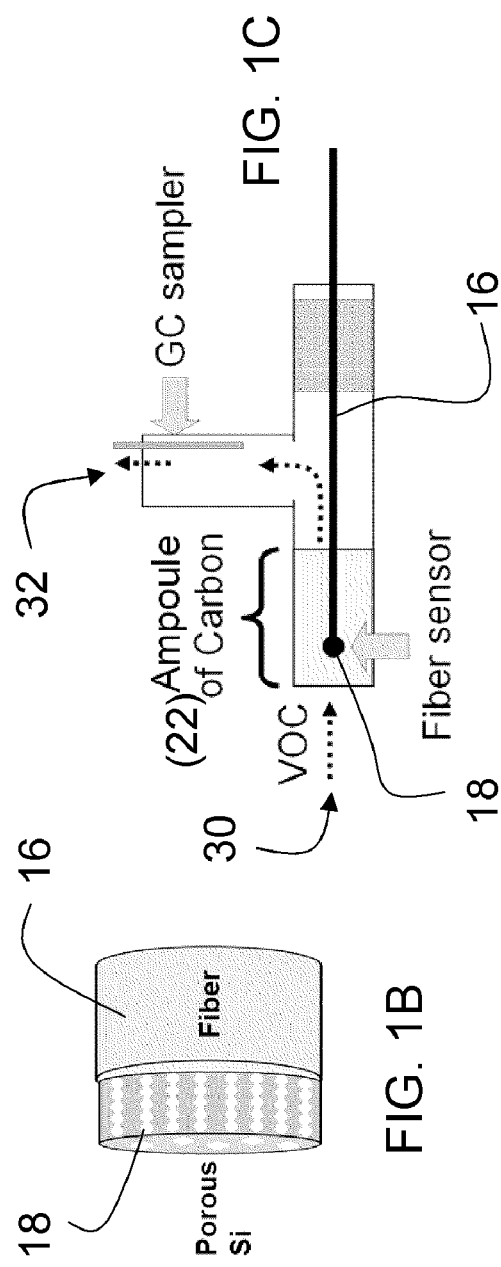

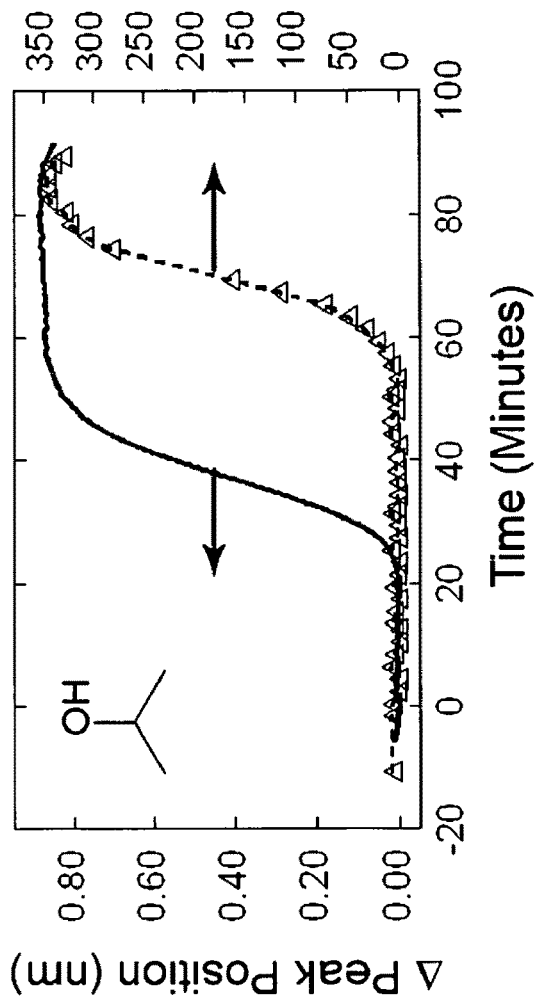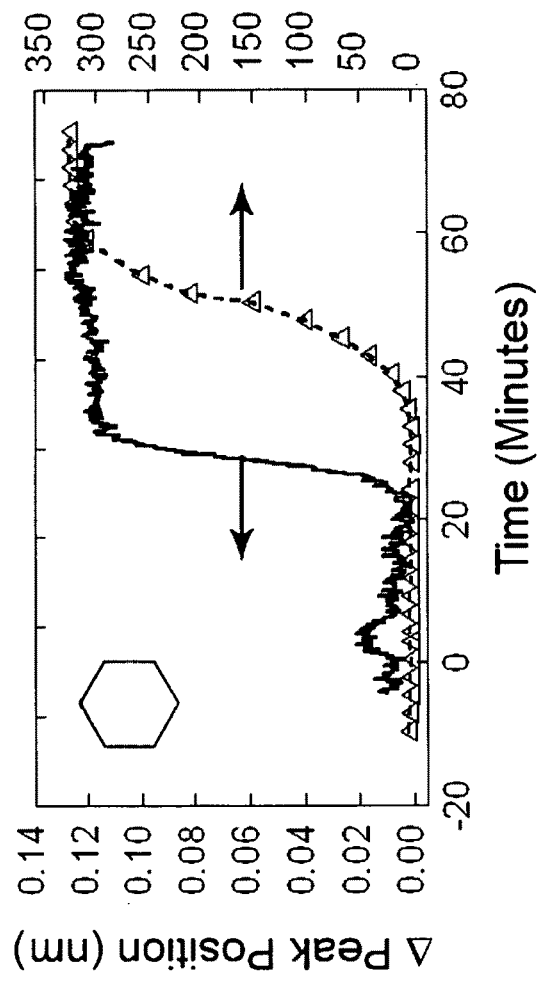
FIG. 3A
FIG. 3B

OPTICAL FIBER-MOUNTED POROUS PHOTONIC CRYSTALS AND SENSORS

CLAIM FOR PRIORITY AND REFERENCE TO RELATED APPLICATION

This application claims priority under 35 U.S.C. §119 from prior provisional application Ser. No. 60/959,210 which was filed Jul. 12, 2007.

STATEMENT OF GOVERNMENT INTEREST

This invention was made with government support under Grant# F49620-02-1-0288 awarded by the Air Force Office of Scientific Research. The government has certain rights in the invention.

FIELD

A field of the invention is sensing. Example applications of the invention include environmental sensing and measurement of humidity, vapor phase chemicals, aqueous chemicals, biomolecules, volatile organic compounds (VOCs), airborne chemical toxins, chemical warfare agents, and toxic industrial chemicals.

BACKGROUND

There is a continual need for low cost, small sized, fast responding sensors for environmental toxins, industrial chemical toxicants and chemical warfare agents. In addition, there is a growing need for sensors that can monitor the residual adsorption capacity of activated carbon filtration cartridges in gas masks and personal protective equipment. In the United States, draft government health and safety regulations require the detection of VOCs prior to depletion of the carbon bed's adsorption capacity. However these regulations have not yet been enacted due to a lack of suitable sensing devices. (NIOSH, *Certification Criteria* 2005, Procedure No. RCT-APR-STP-0066; OSHA, Vol. Standard 1910.134(d)(3)(iii)(B)(2), U.S. Department of Labor, 2006) These sensors would operate by detecting organic vapors breaking through a filter bed of activated carbon.

A number of colorimetric, thermal, and electrical sensors for VOCs have been deployed for carbon filtration bed end-of-service-life applications, each with limited success. Dye-based, passive colorimetric indicators are functionally limited by chemical group selectivity, restricting their utility as broad-class sensors for hazardous compounds like VOCs. Many calorimetric sensors are additionally irreversible, adding to implementation cost.

Thermal sensors measure the local temperature of activated carbon which can rise by several degrees from heat released during adsorption of VOCs. However, thermal sensors for adsorption events are difficult to implement outside of a controlled laboratory setting and are ineffective at detecting the adsorption of small quantities of analyte over longer time periods.

Transconduction sensors measure changes in electrical conduction that result from adsorption of analyte into a conductor or semiconductor. Metal oxide transconduction sensors require large currents to operate at elevated temperatures, and recent chemiresistor and semiconductor transconduction sensors contain supporting electronics that are susceptible to environmental stress. Typical transconduction designs retain a large form factor that is difficult to use inside a respiratory mask carbon bed.

Fiber-optic-based sensors have been applied to a variety of remote sensing problems: measurement of pressure, humidity, vapor-phase chemicals, and aqueous biomolecules are leading examples. With a width of only a few tens to hundreds of microns, these sensors are impervious to electrical interference, require little power to operate, and can be multiplexed together into distributed sensor configurations.

Many fiber optic sensors for organic and water vapors operate by detecting changes in transmitted light intensity. An example of this intensity measurement technique is use of the fluorescence enhancement of an immobilized polymer to detect for organic vapors. See, S. M. Barnard & D. R. Walt, "Fiber-optic Organic Vapor Sensor," Environ. Sci. Technol. 1991, 25, 1301. Another example is the immobilizing of cobalt chloride on a plastic fiber to sense for water vapor in a calorimetric reaction (See, C. M. Tay, et al., "Humidity Sensing Using Plastic Optical Fibers," Proceedings of the SPIE 2004, 5590, 77.) An additional example is the sensing changes in organic solvent refractive indices with surface plasmon resonance at a fiber terminus. (See, H. Suzuki, et al, "Development of a dual-color optical fiber SPR sensor", Sensors, 2005 IEEE, 2005, 865. Fabry-Perot and interferometric sensors have been developed that utilize optical interference effects for optical transduction. These sensors monitor transmitted light intensity induced, for instance, by mechanical changes in a fiber by temperature or pressure. See, e.g., B. Lee, "Review of the Present Status of Optical Fiber Sensors," Optical Fiber Technology 2003, 9, 57; A. Wang, et al, "Fiber-Optic Temperature Sensors based on Differential Spectral Transmittance/Reflectivity and Multiplexed Sensing Systems," Applied Optics 1995, 34, 2295; F. Mitschke, "Fiber-Optic Sensor for Humidity," Optics Letters 1989, 14, 967.

Fibers that were made porous have also been published in the literature. A sensor that coupled a porous fiber with bromothymol blue to monitor transmitted light for ammonia detection has been reported. Q. Zhou, et al,. "Porous Plastic Optical Fiber Sensor for Ammonia Measurement," Applied Optics 1989, 28, 2022. Another study coupled a ruthenium complex to a porous fiber to sense for oxygen by fluorescence quenching. B. D. MacCraith, et al, "Fibre Optic Oxygen Sensor based on Fluorescence Quenching of Evanescent-Wave Excited Ruthenium Complexes in Sol-Gel Derived Porous Coatings," Analyst 1993, 118, 385.

Previous inventions from the Sailor research group at the University of California at San Diego concern the construction of millimeter to micron-sized, nanostructure photonic crystal particles that respond to various organic and inorganic molecules in the vapor phase, including volatile organic compounds and chemical warfare agents. The response of these materials is observed in the form of a characteristic change in the reflection spectrum from the photonic crystals.

SUMMARY OF THE INVENTION

An embodiment of the invention is a remote sensor that has an optical fiber terminating in a tip. A thin film porous particle having a characteristic optical response that changes in the presence of an analyte is optically coupled and physically attached to the tip of the optical fiber. The optical response of the particle changes in the presence of an analyte, and the particle also serves to concentrate analyte. The thin film porous particle can be functionalized toward sensitivity for a predetermined analyte or analytes. A method of remote sensing exposes the remote sensor to an environment to be monitored for analyte. The thin film porous particle is probed with a light source. Reflected light is monitored through the optical fiber for a wavelength shift in the particle's characteristic reflected light spectrum.

BRIEF DESCRIPTION OF THE DRAWINGS

FIGS. 1A-1C show an example system of the invention including a porous photonic crystal tipped optical sensor;

FIG. 3A (for isopropyl alcohol) and 3B (for cyclohexane) illustrate curves (solid, left axes) of a freshly-prepared porous Si tipped optical fiber sensor embedded in a carbon bed ampoule (FIG. 1C), and analyte concentrations determined by gas chromatograph (triangles/dotted, right axes) sampled at the outflow of the carbon bed;

DETAILED DESCRIPTION OF THE PREFERRED EMBODIMENTS

Figures 2A, 2B:
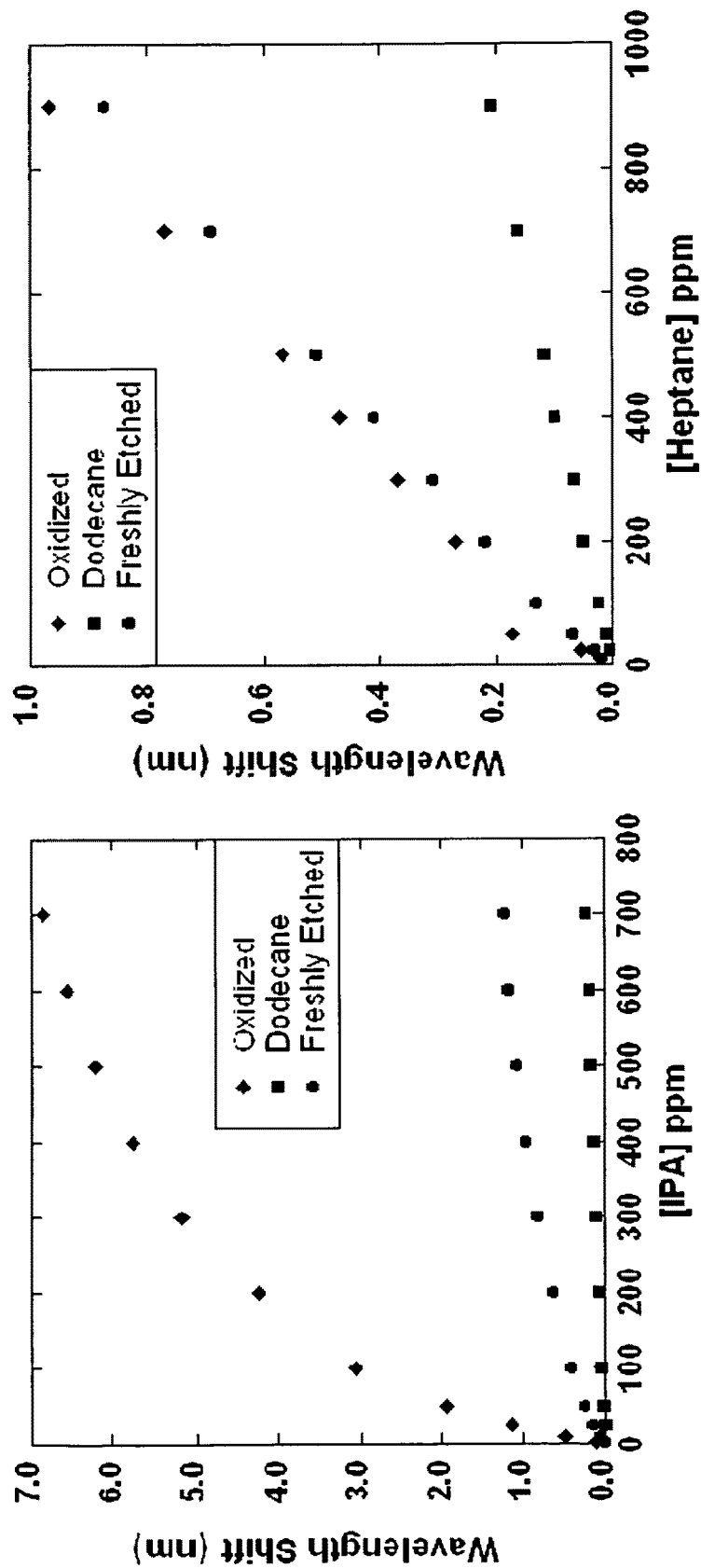
FIG. 2A shows experimental data taken from a system consistent with FIG. 1A illustrating the response of dodecane terminated, oxidized, and freshly-prepared porous silicon tipped optical fibers to IPA at 10-700 ppm
FIG. 2B illustrates the response of oxidized, dodecane terminated, methyl terminated, and freshly etched porous silicon tipped fibers to heptane from 10-900 ppm.

An embodiment of the invention is a remote sensor that has a porous photonic crystal sensor, such as a porous silicon crystal, mounted to the tip of one or more optical fibers to create a small, pinpoint fiber optic based sensor. This remote sensor device has many applictions, for example, environmental sensing and measurement of humidity, vapor phase chemicals, aqueous chemicals and biomolecules.

An embodiment of the invention is a remote sensor that has an optical fiber terminating in a tip. A thin film porous particle having a characteristic optical response that changes in the presence of an analyte is optically coupled and physically attached to the tip of the optical fiber. The optical response of the particle changes in the presence of analyte, and the particle also serves to concentrate analyte. The thin film porous particle can be functionalized toward sensitivity for a predetermined analyte or analytes. A method of remote sensing exposes the remote sensor to an environment to be monitored for analyte. The thin film porous particle is probed with a light source. Reflected light is monitored through the optical fiber for a wavelength shift in the reflected light spectrum.

A particular method uses a remote sensor of the invention to measure for indications of natural resources, e.g., petroleum, methane, or natural gas deposits. A remote sensor is placed in an underground or near-surface region to serve as an indicator of buried or undersea petroleum, methane, or natural gas deposits. The sensor, by wavelength or intensity shift in the reflected spectrum, can detect such deposits.

In preferred systems and methods of the invention, a porous crystal tipped optical fiber sensor senses for analytes by monitoring the wavelength of transmitted light as opposed to the intensity of transmitted light. Transmitted light intensity is susceptible to interference from optical loss, changes in the radius of curvature of the fiber, and mechanical vibrations. These conditions do not affect the wavelength of transmitted light. In addition to producing a reflected light spectrum, the porous crystal tip of the optical fiber provides a microstructure for concentrating analytes. The porous crystal surface can easily be chemically modified, allowing the opportunity for tailorable surface chemistry and VOC preference.

The invention uses preexisting methods of fabricating photonic crystals of porous Si involving: etching a silicon substrate to obtain a patterned layer; and releasing the patterned layer as a freestanding film (See, for example, U.S. Pat. No. 7,318,903, "Photonic Sensor Particles and Fabrication Methods," Link, J. R.; Sailor, M. J., 2008). The film can be treated to impart a surface affinity that is highly hydrophobic, highly hydrophilic, or somewhere in between; treating a porous silicon layer by methods such as thermal oxidation, thermal reaction, photochemical reaction, electrochemical reaction, with alkyllithium reagents, or with acetylene at elevated temperatures have been demonstrated (See, for example, Anglin, E. J., Cheng, L., Freeman, W. R. & Sailor, M. J. Porous Silicon in Drug Delivery Devices and Materials. Adv. Drug Deliv. Rev. 60, 1266-1277 (2008).

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

FIGS. 1A-1C show a remote sensing system of the invention that includes remote sensor 12 that is an optical fiber probe. The remote sensor includes an optical fiber 14 terminating in a tip 16. A thin film porous particle 18 having a characteristic optical response that changes in the presence of an analyte is optically coupled and physically attached to the tip 16 of the optical fiber 14. A light source 19 is optically coupled to the optical fiber 14 to launch a light beam out of the tip 16 of the optical fiber and yield an optical reflected light signal from the thin film porous particle 18 in response to an analyte. An optical sensor 20, e.g., in the form of a CCD spectrometer, is optically coupled to the optical fiber 14 to sense the response of the thin film porous particle 18 via the probe beam from the light source 19. Other optical sensors include simple light sensors, such as photodiodes or phototransisors. Additional electronics quantify the response of the simple light sensors to provide data to measure a frequency or intensity shift, or an intensity shift in one or more particular frequency bands.

The optical sensor 20 preferably measures the response of the thin film porous particle 18. In FIG. 1A, the remote sensor 12 is sensing an activated carbon bed 22 for a break-through event. The remote sensor is periodically or continuously monitored, and the output of the optical sensor can be provided to a computer 24 that includes software for analyzing the response sensed by the optical sensor. In preferred embodiments, the frequency response is measured. Other embodiments measure intensity response. The intensity response can also be measured in one or a number of specific frequency bands. Preferably, the computer also records and stores data received from the optical sensor 20, and can provide a frequency response display 26 or other form of output. While the computer is shown to be a workstation, the optical sensor 20 can itself incorporate hardware and/or software, and can communicate with a laptop, desktop, handheld or other computer by any wired or wireless means and over networks or otherwise.

FIG. 1C shows additional detail of an experimental arrangement using a remote sensor 12 of the invention. The carbon bed 22 was an ampoule of carbon disposed in a VOC (volatile organic compound) inlet 30. The remote sensor was used for frequency analysis by the system as discussed above. Additionally, a VOC outlet 32 was provided to a gas chromatograph, which served as an independent measurement for VOC breakthrough.

The porous particle 18 can be made from various materials, and can have magnetic, hydrophobic, hydrophilic, and other properties. It can also exhibit different types of codes. Porous particles and films constructed from electrochemically etched porous materials have provided powerful methods for labeling and encoding. Preferred embodiments of the invention make use of porous silicon particles. Encoding strategies for forming porous silicon particles can be applicable to other semiconductors and insulators. Preferred porous particles and films and methods of making such particles are disclosed in 1) U.S. Published Patent Application 20050042764, entitled "Optically Encoded Particles" to Sailor et al., published Feb. 24, 2005; 2) U.S. Published Patent Application 20050009374, entitled "Direct Patterning of Silicon by Photoelectrochemical Etching", to Gao, et al., published Jan. 13, 2005; 3) U.S. Published Patent Application 20030146109 entitled "Porous Thin Film Time-Varying Reflectivity Analysis of Samples," to Sailor, et al. published Aug. 7, 2003, now U.S. Pat. No. 7,042,570; 4) PCT Application PCT/US04/043001, entitled "Optically Encoded Particles, System and High Throughput Screening, to Sailor et al, filed Dec. 21, 2004; 5) PCT Application PCT/US04/042997, entitled Optically Encoded Particles with Grey Scale Spectra," to Sailor et al, filed Dec. 21, 2004; 6) U.S. Published Application 20060255508, entitled, "Photonic Sensor Particles and Fabrication Methods", to Sailor, et al filed Aug. 13, 2004, now U.S. Pat. No. 7,318,903; 7) U.S. Published Application 20070051815, entitled "Optically Encoded Particles with Grey Scale Spectra" to Sailor et al, filed Dec. 21, 2004; 8) U.S. Published Application 20070108465, entitled "Porous Microstructure Multi Layer Spectroscopy and Biosensing" to Sailor et al, filed Mar. 8, 2006; 9) U.S. Published Application 20070148695 entitled "Optically Encoded Particles, System and High-Throughput Screening" to Sailor et al., filed Dec. 21, 2004; and 10) U.S. Published Application 20080145513 entitled "Polymer Composite Photonic Particles" to Sailor et al. filed Dec. 14, 2005.

In general, porous particles that have a characteristic optical response that changes in the presence of analyte can be used. Additionally, particles can be treated to have a specific affinity for particular analytes of interest, such as with binding agents or through hydrophobic or hydrophilic nature of the particles.

To demonstrate the invention and test sensitivity, remote sensing with optical fiber mounted porous silicon crystals in accordance win the system shown in FIGS. 1A-1C has been conducted in experiments. A first set of experiments concerned detection of volatile organic compound (VOC) breakthrough of an activated carbon bed. In a second set of experiments, fiber sensors of the invention were employed in activated carbon filtration beds used in respiratory masks and characterized for VOC breakthrough detection. A particular preferred embodiment of the device is a respiratory mask with an embedded optical fiber sensor.

The experiments will be described and will be illustrative of additional preferred embodiment devices and methods, as well as broader aspects of the invention. Artisans will recognize additional features and applications of the invention from the following description. In the experiments, silicon nanoporous crystal sensors were attached to optical fibers. Other nanoporous semiconductors and insulators can also be used.

The experimental configuration that was used to demonstrate the invention was consistent with FIGS. 1A-1C. Porous Si samples displaying a single spectral reflectance peak were prepared from single crystal, (100)-oriented highly boron-doped p-type Si by electrochemical etching in a 3:1 v:v solution of aqueous hydrofluoric acid:ethanol (49% hydrofluoric acid). The porous layer was detached from the bulk Si by applying a current of 2.7 $mA/cm^2$ for 2 minutes in a 3.3% hydrofluoric acid:ethanol solution. The photonic crystals were attached to the tip of multimode optical fibers using adhesive.

The reflectivity spectrum of the porous Si layer was monitored for sensing events. When the porous Si film is exposed to analyte, analyte adsorbs to the pore walls. This interaction causes a change in the average index of refraction of the film, which produces a shift of the reflected light spectrum.

The freshly-prepared porous Si films are hydrogen-terminated, although the processing steps generate a mixed hydride-oxide surface. This surface is relatively hydrophobic. Additional porous Si films were etched followed by a chemical modification reaction to alter the surface properties of the films. Separate chemical modifications included oxidation of the sample in a tube furnace at 600° C. for 90 minutes, thermal hydrosilylation in neat 1-dodecene, electrochemical methylation, halogenation followed by methylation, silanization with dichlorodimethylsilane, and reaction with acetylene at elevated temperatures. These reactions produced films that were either more hydrophilic or more hydrophobic than the freshly-prepared porous Si.

FIG. 2A shows experimental sensor calibration data taken from a system consistent with FIG. 1A but without the carbon bed (22). illustrating the response of dodecane terminated, oxidized, methyl terminated, and freshly-prepared porous silicon tipped optical fibers to IPA at 10-700 ppm and FIG. 2B illustrates the response of oxidized, dodecane terminated, and freshly etched porous silicon tipped fibers to heptane. The freshly-prepared sample was additionally calibrated to exposures of cyclohexane and trichloroethylene. Results indicate that the porous Si films are sensitive to low concentrations of volatile organic compounds (VOCs). The results also show that the response of the porous, thin film, photonic crystal-tipped fiber can be influenced towards particular classes of analytes, e.g., particular VOCs through chemical modification of the porous surface. The response can be tailored toward sensitivity to a predetermined analyte or plurality of analytes.

Remote sensing with the optical fiber-mounted porous Si photonic crystal was also tested by detecting breakthrough of VOCs in a small volume activated carbon filtration bed. A stream of analyte was flown through a glass ampoule containing activated carbon. The ampoule outflow was connected to a plastic T-junction as illustrated in FIG. 1C, which connected the ampoule effluent to a gas chromatograph. The porous Si-tipped fiber was packed into the middle of the carbon bed. A steady flow of analyte was introduced to the ampoule. FIG. 3A (for isopropyl alcohol) and 3B (for cyclohexane) illustrate curves (solid, left axes) of a freshly-prepared porous Si tipped optical fiber sensor embedded in a carbon bed ampoule, and analyte concentrations determined by gas chromatograph (triangles/dotted, right axes) sampled at the outflow of the carbon bed. Analyte concentration in the carrier stream is 300 ppm. In each trial, the implanted sensor responded to analyte in advance of detection by the gas chromatograph. This result showed that the porous Si coupled fiber successfully sensed breakthrough of analyte in a carbon bed, thus acting as an end-of-service-life indicator and a remote sensor.

Freshly-prepared porous Si sensors used in the experiments that provided the FIGS. 3A and 3B data were exposed to analyte in a 0% relative humidity (RH) environment. Sensors in a 63% RH environment experienced a slight increase in signal change due to the presence of water. Results have shown that the porous Si response to water can be amplified through thermally oxidizing the sample surface. Alternatively, the response to water can be further limited by preparing a sample with covalently attached hydrophobic hydrocarbons. For the end-of-service-life application however, the sensor's response to water vapor does not entirely detract from its applicability; regardless of whether the carbon bed adsorbs water vapor or toxic VOCs, depletion of its adsorption capacity greatly reduces the efficiency of the activated carbon in protecting its user.

Breakthrough experiments were also performed using a second system which more closely mimicked a commercial respiratory carbon bed filtration pack. A carbon bed simulator was built at NIOSH (National Institute of Occupational Safety and Health). The simulator consisted of a sealed air flow chamber that held a vessel the size of a personal respirator carbon filtration cartridge. A large, sealable chamber contained a smaller flow through vessel inside. The vessel was filled with 50 grams of activated carbon, the same weight of carbon that is used in a commercial filter pack. Air containing analyte was introduced to the chamber and flowed through the vessel. Gas chromatograph probes for monitoring analyte concentration were placed at middle carbon bed height, and at the carbon bed exit at the top. The 50 grams of carbon in the vessel mimicked a filter pack found in respiratory masks.

Figure 4:
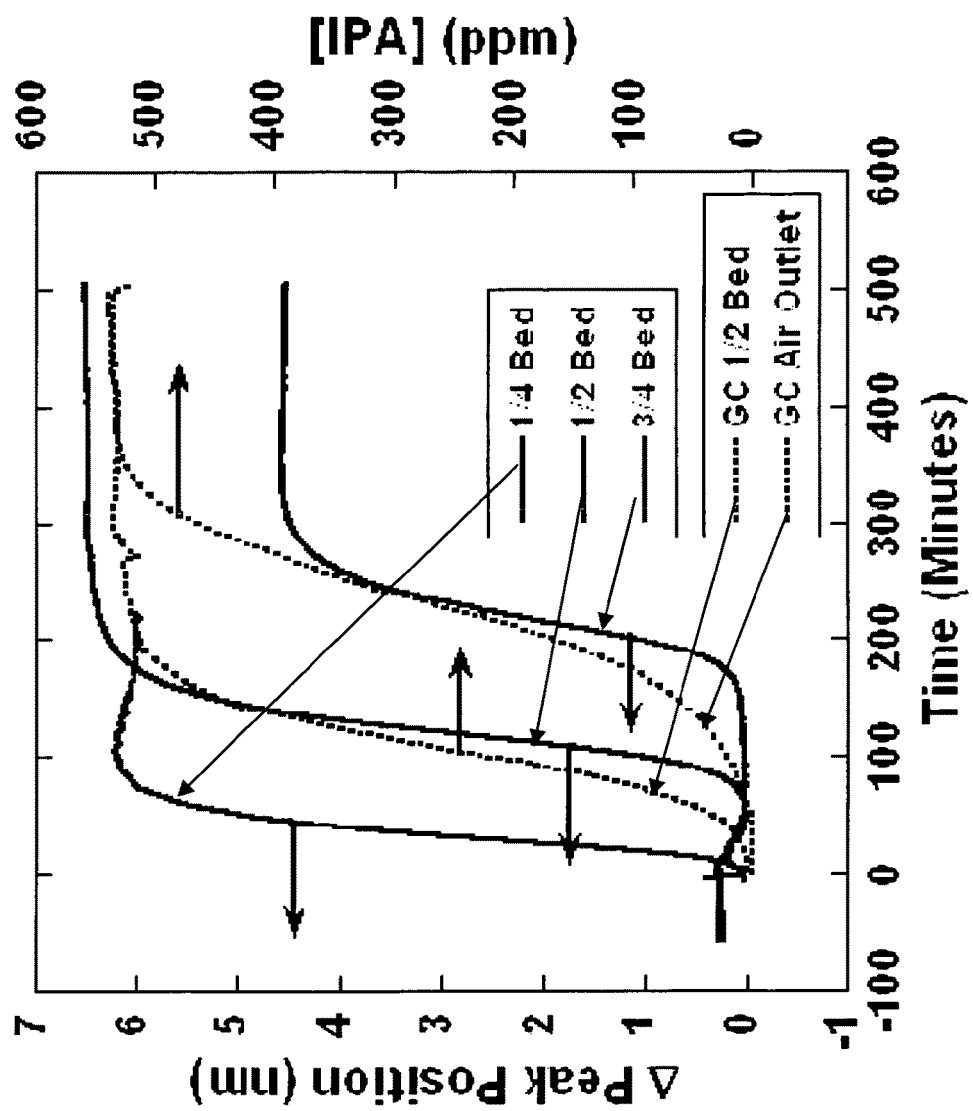
FIG. 4 illustrates results from monitoring carbon bed breakthrough of 500 ppm IPA with oxidized porous silicon-tipped optical fibers positioned at various heights in the carbon bed.

Oxidized porous silicon tipped fibers were placed in the carbon filter bed at ¼, ½, and ¾ bed height in order to monitor the breakthrough of analyte as it traversed the carbon bed. The analyte used was isopropyl alcohol at a steady concentration of 500 ppm. By monitoring the reflectivity peak position of the porous silicon on the three fibers, the breakthrough of analyte was observed. As expected, the ¼ height fiber responded first, followed by the ½ and the ¾ height fibers. IPA concentration was monitored by a GC at ½ carbon bed and at the air outlet. Results are shown in FIG. 4.

Figure 5:
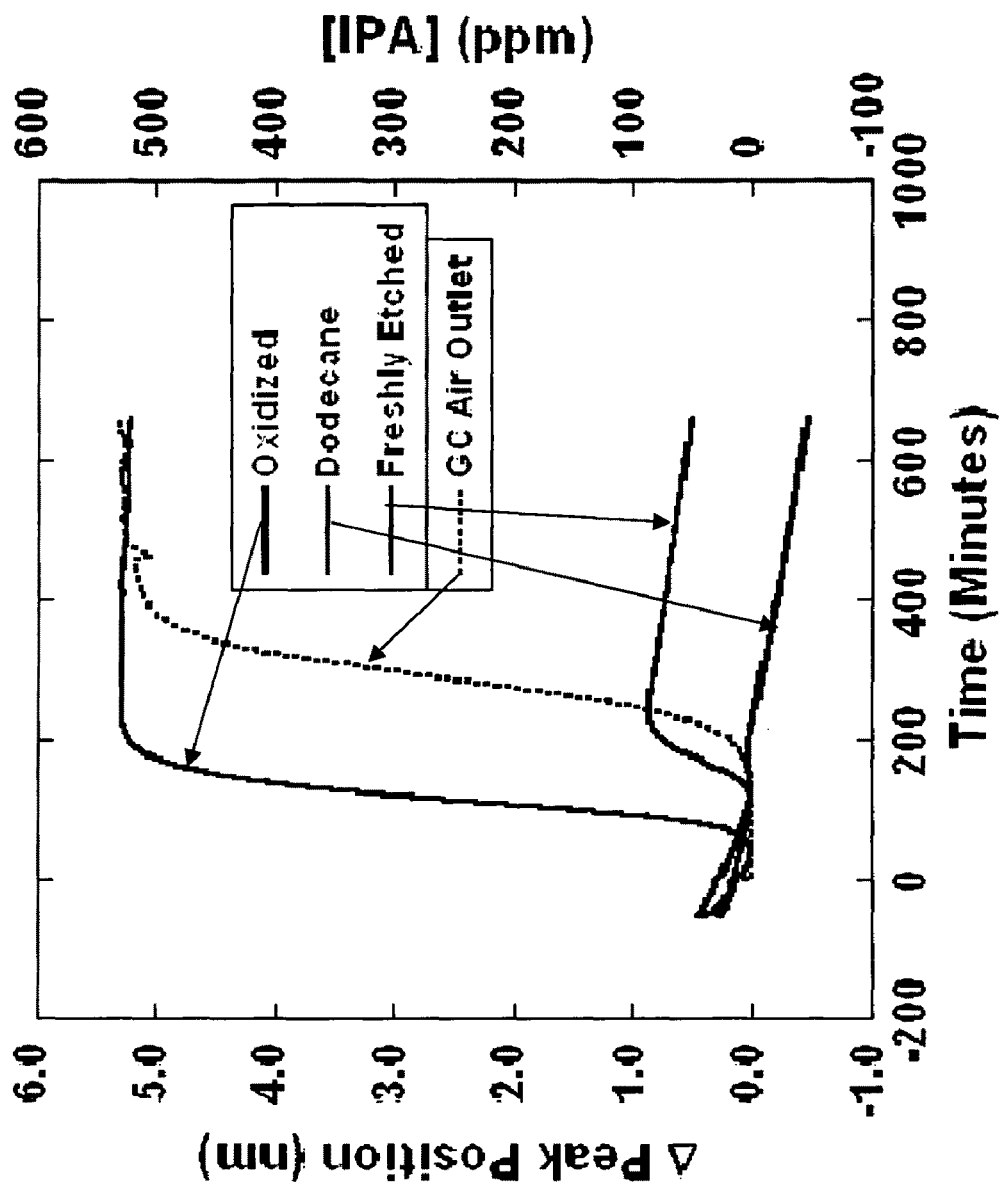
FIG. 5 illustrates results from carbon bed breakthrough with IPA monitored by three fibers implanted at ½ carbon bed height.

Breakthrough of 500 ppm IPA was also monitored with fibers of various surface chemistries. Three fibers tipped separately with porous silicon that was freshly etched (hydride terminated), oxidized, and dodecane-terminated were placed at ½ carbon bed height. The response of the fibers is shown in FIG. 5. As expected from the data in FIG. 2A, the oxidized porous silicon tipped fiber had the largest response, followed by the freshly etched hydride terminated, and lastly by the dodecane terminated. The same three fibers were used to monitor carbon bed breakthrough of 500 ppm heptane. The response was as predicted by the data in FIG. 2B. Heptane carbon bed breakthrough (500 ppm) was additionally performed under pulsed analyte/air flow. A pulsed pumped was used to mimic human breathing. The pulsed breather breakthrough time was the same as for the constant flow breakthrough.

Figure 6:
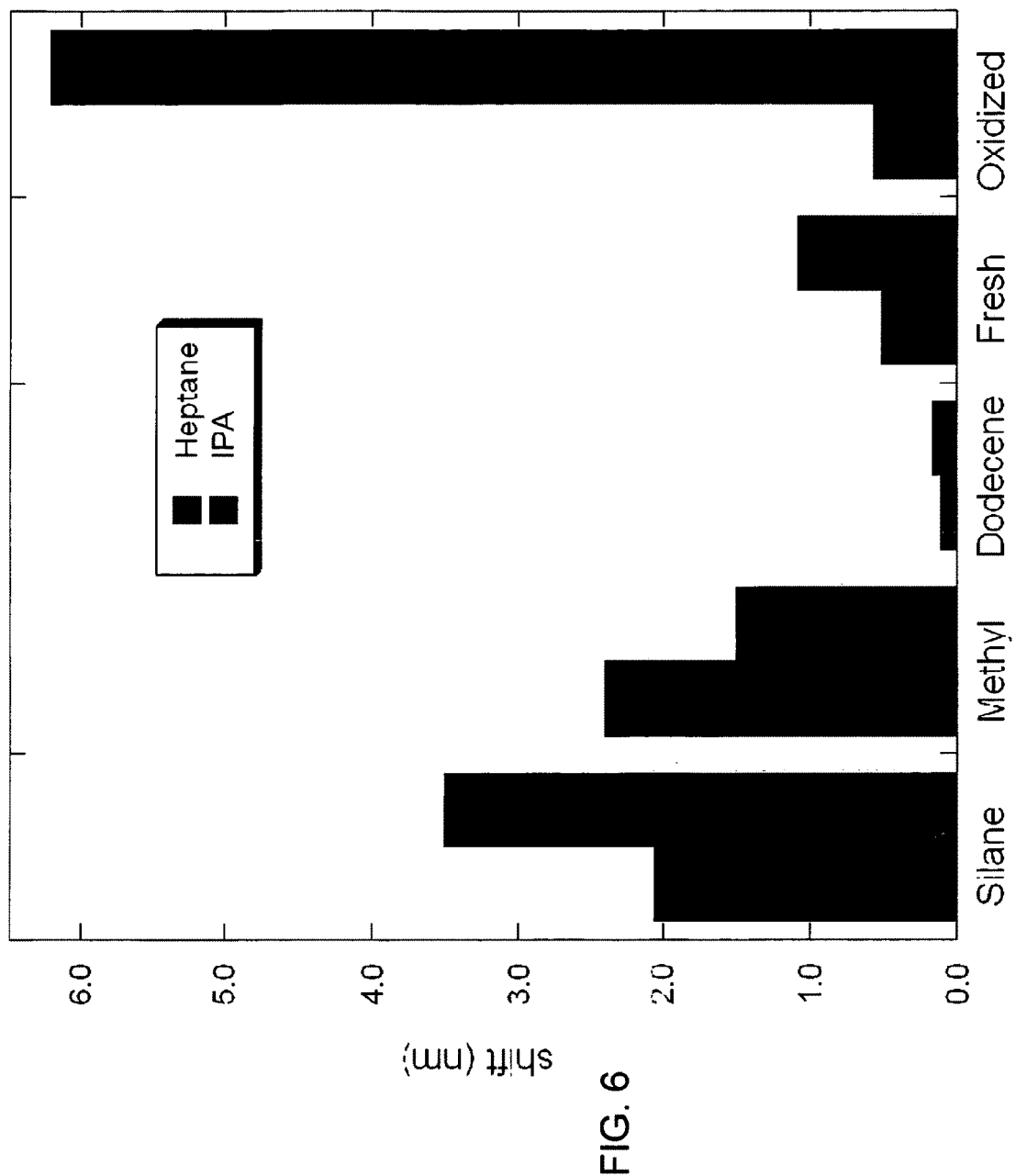
FIG. 6 illustrates the reflectivity wavelength shift of chemically modified porous silicon tipped fibers to 500 ppm of heptane and 500 ppm of IPA.

Additional chemical modifications were also tested on dimethyl silane and methyl-terminated porous silicon sensor fibers. The response of the silane and methylated porous sensor tipped fibers to 500 ppm of heptane (left) and IPA (right) is shown in FIG. 6. The oxidized porous crystal sensor tipped fibers exhibited the largest shift in response to IPA, while the methylated porous crystal tipped sensor fibers exhibited the largest shift in response to Heptane. The silane terminated crystal showed a strong shift responsive to both IPA and Heptane.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A remote sensor system, comprising:
   a remote sensor comprising an optical fiber terminating in a tip and a thin film porous particle having a characteristic optical response that changes in the presence of an analyte, the thin film porous particle being optically coupled and physically attached to said tip;
   a light source optically coupled to said optical fiber to launch light out said tip;
   an optical sensor comprising a spectrometer optically coupled to said optical fiber to sense the optical frequency response of said thin film porous particle to said light; and
   a computer including software for analyzing the frequency response sensed by the spectrometer to determine changes in the presence of the analyte.

2. The system of claim 1, wherein said optical sensor further senses the intensity of light reflected from said thin film porous particle.

3. The system of claim 2, wherein said optical sensor senses the intensity of light in one or more spectral frequency bands.

4. The system of claim 1, wherein said computer records and stores data received from said spectrometer.

5. The system of claim 1, wherein said optical sensor further comprises a light sensor, and said system further comprises electronics for quantification of the intensity of light sensed by the light sensor.

6. The system of claim 5, wherein said light sensor comprises one of a photodiode or a phototransistor.

7. The system of claim 1, having the optical fiber tip disposed to detect analytes in a surrounding environment.

8. The system of claim 1, having the optical fiber tip disposed in an activated carbon filtration bed to detect the presence of analytes.

9. The system of claim 1, having the optical fiber tip disposed in an activated carbon filtration bed to serve as an end-of-service-life indicator.

10. The sensor of claim 1, wherein said thin film porous particle is physically attached to said tip by adhesive.

11. The sensor of claim 1, wherein said thin film porous particle comprises a silicon thin film porous particle.

12. The sensor of claim 11, wherein said silicon thin film porous particle comprises an oxidized silicon thin film porous particle.

13. The sensor of claim 11, wherein said silicon thin film porous particle comprises a dodecane terminated silicon thin film porous particle.

14. The sensor of claim 1, wherein said thin film porous particle is functionalized toward sensitivity for a predetermined analyte.

15. The sensor of claim 1, wherein said optical fiber comprises a multi-mode optical fiber.

16. A method of remote sensing, the method comprising steps of:

exposing a remote sensor of claim 1 to an environment to be monitored for analyte;
probing the thin film porous particle with light from said light source; and
monitoring reflected light with said optical sensor through the optical fiber for a wavelength shift.

17. The method of claim 16, wherein the environment to be monitored comprises underground or near-surface region to serve as an indicator of buried or undersea petroleum, methane, or natural gas deposits.

\* \* \* \* \*

UNITED STATES PATENT AND TRADEMARK OFFICE
CERTIFICATE OF CORRECTION

Page 1 of 1

PATENT NO. : 7,889,954 B2
APPLICATION NO. : 12/218330
DATED : February 15, 2011
INVENTOR(S) : Sailor et al.

It is certified that error appears in the above-identified patent and that said Letters Patent is hereby corrected as shown below:

Col. 1, line 50    Please delete "calorimetric" and insert --colorimetric-- in its place.

Signed and Sealed this
Sixteenth Day of August, 2011

David J. Kappos
*Director of the United States Patent and Trademark Office*